(12) United States Patent
Tasca et al.

(10) Patent No.: US 10,463,915 B2
(45) Date of Patent: Nov. 5, 2019

(54) SYSTEM, METHOD AND PROGRAM PRODUCT FOR MONITORING THE USE OF AN EXERCISE BALL BY A USER AND EXERCISE BALL WHICH CAN BE USED IN SUCH A SYSTEM

(71) Applicant: TECHNOGYM S.P.A, Cesena (IT)

(72) Inventors: Ermanno Tasca, Cesena (IT); Cristiano Sarti, Cesena (IT); Silvano Zanuso, Cesena (IT); Andrea Leonardi, Cesena (IT); Daniele Cei, Cesena (IT)

(73) Assignee: TECHNOGYM S.P.A., Cesena (IT)

( * ) Notice: Subject to any disclaimer, the term of this patent is extended or adjusted under 35 U.S.C. 154(b) by 22 days.

(21) Appl. No.: 15/209,078

(22) Filed: Jul. 13, 2016

(65) Prior Publication Data

US 2017/0021229 A1    Jan. 26, 2017

(30) Foreign Application Priority Data

Jul. 24, 2015    (IT) .......................... 102015000037781

(51) Int. Cl.
*A63B 24/00*    (2006.01)
*G06F 19/00*    (2018.01)
(Continued)

(52) U.S. Cl.
CPC .......... *A63B 24/0062* (2013.01); *A63B 23/12* (2013.01); *A63B 24/0021* (2013.01);
(Continued)

(58) Field of Classification Search
CPC . A63B 24/00; A63B 24/0062; A63B 24/0087; A63B 24/0021; A63B 39/06;
(Continued)

(56) References Cited

U.S. PATENT DOCUMENTS

2008/0220948 A1 * 9/2008 Publicover ............. A63B 41/00
    482/77
2012/0058845 A1 * 3/2012 Crowley ................ A63B 41/00
    473/604
(Continued)

FOREIGN PATENT DOCUMENTS

CN    101972536 A    2/2011
CN    103269756 A    8/2013
(Continued)

OTHER PUBLICATIONS

International Search Report for ITUB20152459 dated Feb. 10, 2016.

*Primary Examiner* — Nyca T Nguyen
(74) *Attorney, Agent, or Firm* — Arent Fox LLP; Michael Fainberg

(57) ABSTRACT

Disclosed are an exercise ball as well as a system, method and computer program product for monitoring the use of the exercise ball by a user. An exemplary system comprises: a first data processing unit; an exercise ball comprising a shell and a monitoring unit operatively associated with the shell, said monitoring unit comprising at least one sensor for detecting a parameter representative of the movement of the exercise ball by the user, the first data processing unit being configured to determine and provide the user with data representative of the use of the exercise ball by the user based on parameters representative of the movement of the exercise ball by the user detected by said at least one sensor.

18 Claims, 3 Drawing Sheets

(51) Int. Cl.
*A63B 39/06* (2006.01)
*G16H 20/30* (2018.01)
*A63B 41/00* (2006.01)
*A63B 23/12* (2006.01)

(52) U.S. Cl.
CPC .......... *A63B 39/06* (2013.01); *G06F 19/3481* (2013.01); *G16H 20/30* (2018.01); *A63B 41/00* (2013.01)

(58) Field of Classification Search
CPC . A63B 23/12; A63B 19/3481; A63B 37/0056; A63B 37/0098; A63B 41/00; A63B 2041/005; G06F 19/2481; A47C 4/54
See application file for complete search history.

(56) References Cited

U.S. PATENT DOCUMENTS

2013/0296140 A1* 11/2013 Publicover ............ A63B 41/00 482/77

2014/0222177 A1* 8/2014 Thurman ........... G09B 19/0038 700/92
2014/0342329 A1* 11/2014 Debenedetto ....... H04M 1/7253 434/247
2015/0182810 A1* 7/2015 Thurman ............. A63B 43/004 473/570
2015/0217922 A1* 8/2015 Houvener ............. A45C 11/00 206/592
2016/0001136 A1* 1/2016 King .................. A63B 69/0071 320/108

FOREIGN PATENT DOCUMENTS

| | | |
|---|---|---|
| CN | 103298527 A | 9/2013 |
| EP | 1816547 A1 | 8/2007 |
| EP | 2650807 A1 | 10/2013 |
| WO | 99051309 A1 | 10/1999 |
| WO | 2011070138 A1 | 6/2011 |

* cited by examiner

SYSTEM, METHOD AND PROGRAM PRODUCT FOR MONITORING THE USE OF AN EXERCISE BALL BY A USER AND EXERCISE BALL WHICH CAN BE USED IN SUCH A SYSTEM

CROSS-REFERENCE TO RELATED APPLICATIONS

This application claims benefit of priority under 35 U.S.C. 119(a)-(d) to Italian Patent Application No. 102015000037781, filed on Jul. 24, 2015, which is incorporated by reference herein.

FIELD OF TECHNOLOGY

The present invention relates to the field of fitness, and more specifically to a system, method and program product for monitoring the use of an exercise ball by a user and to an exercise ball which can be used in such a system.

BACKGROUND

As is known, an exercise ball is now a common exercise equipment which can be used by a user both for physical activity with the purposes of regular training or rehabilitation and simply as a seat.

Nowadays, the need is however strongly felt to monitor the use of an exercise ball by a user, whether it is used for physical activity or simply as a seat, in order to provide the user with a useful indication, also in real time, about the use of such an exercise equipment and the results which from a physical viewpoint are obtained with such a use.

SUMMARY

It is the object of the present invention to devise and provide a system for monitoring the use of an exercise ball by a user, which allows to at least partially obviate the drawback indicated above with reference to the known art.

Such an object is achieved by means of an exercise ball as well as a system, method and computer program product for monitoring the use of the exercise ball by a user. An exemplary system comprises: a first data processing unit; an exercise ball comprising a shell and a monitoring unit operatively associated with the shell, said monitoring unit comprising at least one sensor for detecting a parameter representative of the movement of the exercise ball by the user, the first data processing unit being configured to determine and provide the user with data representative of the use of the exercise ball by the user based on parameters representative of the movement of the exercise ball by the user detected by said at least one sensor.

BRIEF DESCRIPTION OF THE DRAWINGS

Further features and advantages of the system for monitoring the use of an exercise ball by a user according to the invention will become apparent from the following description of preferred embodiments thereof, given only by way of non-limiting, indicative example, with reference to the accompanying drawings, in which.

DETAILED DESCRIPTION

Figure 1:
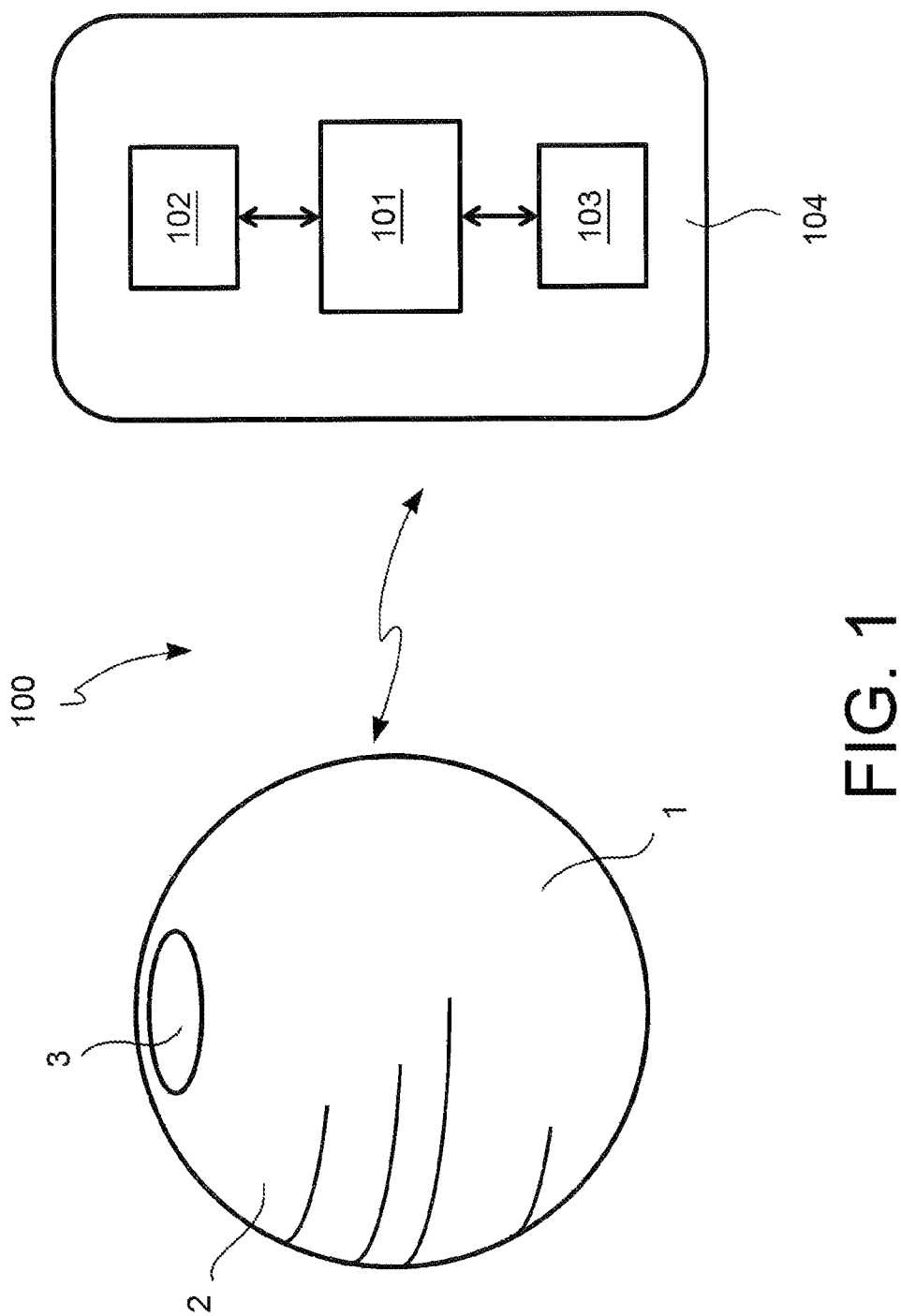
FIG. 1 shows, by means of a block diagram, a system for monitoring the use of an exercise ball by a user in accordance with one embodiment of the invention.

FIG. 1 shows a system 100 for monitoring the use of an exercise ball by a user, hereinafter also simply system 100, according to one embodiment of the invention.

It is worth noting that equal or similar elements in the drawings are indicated with the same number and/or letter.

For the purposes of the present description, "use of an exercise ball by a user" means both the use of the exercise ball as an exercise equipment, and therefore for performing physical exercise in accordance with a specific training or rehabilitation program, and the use of the exercise ball as a normal seat, therefore for improving posture and performing exercises for muscle reinforcement and balance.

With particular reference to the embodiment in FIG. 1, the system 100 comprises a first data processing unit 101, for example a microprocessor or a microcontroller.

The system 100 further comprises a first memory unit 102, operatively connected to the first data processing unit 101.

The first memory unit 102 may be internal or external (such as e.g. shown in FIG. 1) to the first data processing unit 101.

It is worth noting that the first memory unit 102 is configured to store a program product which is executable by the first data processing unit 101 for monitoring the use of an exercise ball by a user, as will be described later.

To this end, the exercise ball, indicated as a whole with numeral 1 in FIG. 1, will be described later with particular reference to FIGS. 1 and 2.

Returning to FIG. 1, the system 100 further comprises a first data communication module 103, operatively connected to the first data processing unit 101, that is adapted to communicate data by means of a data communication channel of the wireless type (for example, by means of a Bluetooth data communication channel, an NFC data communication channel or a Wi-Fi data communication channel).

To this end, as reiterated later, the first data processing unit 101 is advantageously configured to determine data representative of the use of the exercise ball 1 by the user based on parameters representative of the movement of the exercise ball 1 by the user, detected by at least one sensor (described below), and to provide such determined data to the user.

The data representative of the use of the exercise ball 1 by the user and the parameters representative of the movement of the exercise ball 1 by the user will be described later.

Returning to the embodiment in FIG. 1, the system 100 further comprises an electronic device 104 which can be associated with the user (for example a smartphone, a tablet or a multimedia digital file reader, a computer, a notebook or a personal computer, etc.).

In this embodiment, the first data processing unit 101, the first memory unit 102 and the first data communication module 103 are integrated into the electronic device 104.

Such an electronic device 104 is shown in FIG. 1 as a smartphone.

As introduced above, the system 100 further comprises an exercise ball 1, which will now be described with particular reference to FIGS. 1 and 2.

With reference to FIG. 1, the exercise ball comprises a shell 2.

The shell 2, for example made of plastic material, is preferably spherical in shape.

In particular, the shell 2 comprises a hole (not shown in the figures) through which pressurized air may be introduced into the shell 2. Such a hole is provided with a suitable closing valve (also not shown in the figures) so that the shell 2 filled with air may keep its shape.

Moreover, such a closing valve is provided with a plug, the removal of which allows to adjust the pressure of the air inside the shell 2 so as to inflate/deflate the exercise ball 1.

In addition, in accordance with one embodiment, the shell 2 may also comprise a stabilizing element adapted to allow the exercise ball 1 to rest on the floor always with the same portion, which may be obtained by manufacturing a portion of the exercise ball 1 with a second plastic material of different density, or with a greater thickness (exercise ball with double density) or by introducing a counterweight into the shell 2 in correspondence with the portion intended to rest on the floor.

The exercise ball 1 further comprises a monitoring unit 3 for the use of the exercise ball 1 by a user, hereinafter also simply called monitoring unit 3, operatively associated with the shell 2.

In the embodiment in FIG. 1, the monitoring unit 3 is integrated into the shell 2 of the exercise ball 1.

In particular, in one embodiment, the monitoring unit 3 may be advantageously associated with, or integrated into the portion of the shell 2 of the exercise ball 1 in which there is the hole with the respective closing valve. This portion of the shell 2 typically has an increased rigidity with respect to the rest of the shell 2 and, in this portion, the deformation of the shell 2 due to the action of the user is not very consistent.

In greater detail, in accordance with a further embodiment, the monitoring unit 3 may be associated with, or integrated into the closing valve of the hole of the shell 2.

In another embodiment, alternative to the one described above, the monitoring unit 3 may be associated with or integrated into a further portion of the shell 2, different from the portion of the shell 2 in which there is the hole with the respective closing valve. In such a further portion, which is typically far from the portion of the shell 2 in which there is the hole with the respective closing valve, the deformation of the shell 2 of the exercise ball 1 due to the action of the user is more consistent.

In a further embodiment, not shown in FIG. 1, the exercise ball 1 may comprise a cover of the shell 2.

Such a cover is for example made of fabric and has one or more portions further covered with a non slip material. The cover comprises an opening with a strap or hinge closure for accommodating and keeping the shell 2 of the exercise ball 1 inside the cover.

In a further embodiment (not shown in the figures), alternative to the one in which the monitoring unit 3 is integrated into the shell 2 of the exercise ball 1, the monitoring unit 3 may be integrated into the cover of the shell 2 of the exercise ball 1.

To this end, in one embodiment, the monitoring unit 3 may be advantageously associated with or integrated into a portion of the cover intended to cover the portion of the shell 2 of the exercise ball 1 in which there is the hole with the respective closing valve.

In another embodiment, alternative to the one described above, the monitoring unit 3 may be associated with or integrated into a further portion of the cover, different from the portion intended to cover the portion of the shell 2 in which there is the hole with the respective closing valve, at which the deformation of the shell 2 due to the action of the user is more consistent.

Such a further portion of the cover may be near the opening with strap or hinge closure.

In a further embodiment, alternative to the preceding ones, the monitoring unit 3 may comprise a first portion integrated into the shell 2 of the exercise ball 1, and a second portion integrated into the cover of the shell 2 of the exercise ball 1.

Figure 2:
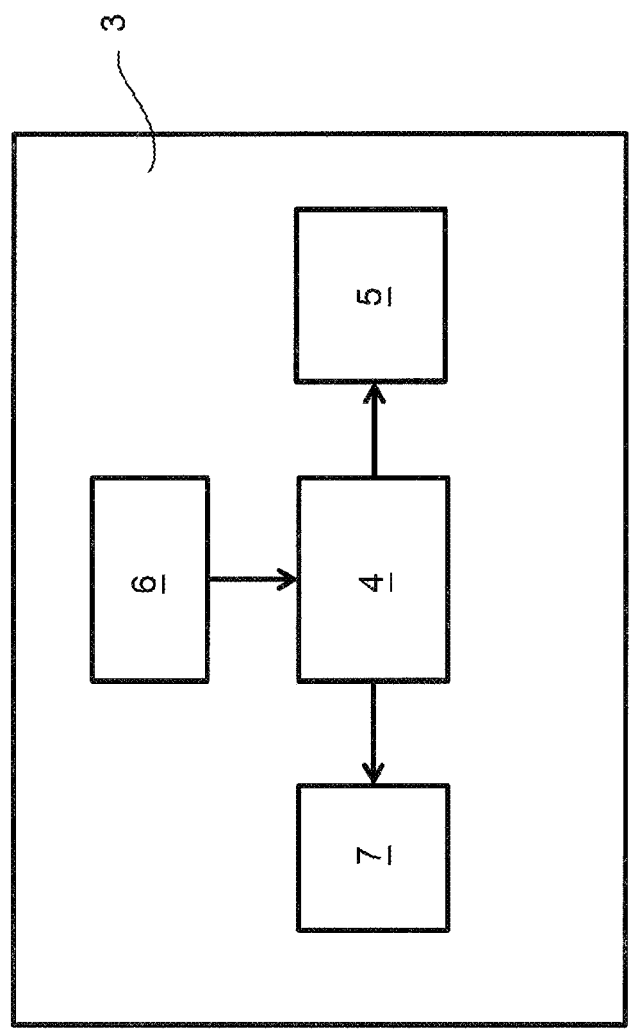
FIG. 2 shows, by means of a block diagram, a component of an exercise ball in accordance with one embodiment of the invention.

With reference to the block diagram in FIG. 2, the monitoring unit 3 for monitoring the use of the exercise ball 1 by a user in accordance with one embodiment of the invention is now described.

The monitoring unit 3 may be made for example, on a printed circuit (not shown in the figures).

The monitoring unit 3 comprises a second data processing unit 4, for example a microprocessor or a microcontroller.

The monitoring unit 3 further comprises a second memory unit 5, operatively connected to the second data processing unit 4. Also in this case, the second memory unit 5 may be internal or external (as shown in FIG. 2) with respect to the second data processing unit 4.

It is worth noting that the second memory unit 5 is configured to store a program product which is executable by the second data processing unit 4 for generating data representative of the use of the exercise ball 1 by a user, which are described later.

To this end, the monitoring unit 3 further comprises at least one sensor 6 for detecting a parameter representative of the movement of the exercise ball 1 by the user.

Such at least one sensor 6 is operatively connected to the second data processing unit 4.

For the purposes of the present description, "parameter representative of the movement of the exercise ball by a user" means both a parameter representative of the movement of the exercise ball such as, for example, the acceleration, speed, rotation, etc., and a parameter representative of the deformation of the shell under the action of the user, whether it is voluntary (during a specific physical exercise) or involuntary (e.g. during sitting) by the user such as for example, extension, pressure, etc.

Thus, in accordance with various embodiments, the at least one sensor 6 will be chosen conveniently for detecting the parameter selected based on the selection of the parameter representative of the movement of the user during the use of the exercise ball 1.

If the parameter to be detected is a parameter representative of the movement of the exercise ball, such at least one sensor 6 may be an accelometer, gyroscope, a combination of the two, etc.

If the parameter to be detected is a parameter representative of the deformation of the shell under the action of the user, the at least one sensor 6 may be an extensometer, pressure sensor, a combination of the two, etc.

In particular, if the monitoring unit 3 is associated with or integrated into the portion of the shell 2 of the exercise ball 1 in which there is the hole with the respective closing valve or into the portion of the cover intended to cover the portion of the shell 3 of the exercise ball 1 in which there is the hole with the respective closing valve, such an at least one sensor 6 is preferably a pressure sensor.

In another embodiment, if the monitoring unit 3 is associated with or integrated into a further portion of the shell 2 which is different from the portion of shell 2 in which there is the hole with the respective closing valve or into a further portion of the cover different from the portion intended to cover the portion of the shell 2 in which there is the hole with the respective closing valve, such at least one sensor 6 is preferably a deformation sensor.

In accordance with a further embodiment, not shown in the figures, the exercise ball 1 may comprise a plurality of sensors, each for detecting a parameter representative of the movement of the exercise ball 1 by the user.

If the plurality of sensors comprises a plurality of deformation sensors, such a plurality is distributed over several portions of the shell 2 (or of the cover of the shell 2, when present) subjected to increased deformation, in which the action due to the user is consistent.

Returning again to FIG. 2, the monitoring unit 3 in one embodiment comprises a second data communication module 7 adapted to communicate data by means of a data communication channel of the wireless type (for example, by means of a Bluetooth data communication channel, an NFC data communication channel or a Wi-Fi data communication channel).

In particular, such a data communication module 7 is adapted to communicate such a parameter representative of the movement of the exercise ball 1 by the user to the first data processing unit of the system 100, by means of the data communication channel of the wireless type.

The data communication module 7 is operatively connected to the second data processing unit 4.

It is worth noting that the second data processing unit 4 is configured to communicate the value of the parameter detected by said at least one sensor 6 to the first data processing unit 101 of the system 100, by means of the second data communication module 7.

In greater detail, the second data processing unit 4 is configured to communicate the value of the parameter detected by said at least one sensor 6 to the first data communication module 103 of the system 100, therefore to the first data processing unit 101, by means of the second data communication module 7.

The first data processing unit 101 is advantageously configured to determine data representative of the use of the exercise ball 1 by the user based on parameters representative of the movement of the exercise ball 1 by the user detected by said at least one sensor 6.

Moreover, as already mentioned above, the first data processing unit 101 is advantageously configured to provide the user with the determined data representative of the use of the exercise ball 1 by the user.

"Data representative of the use of the exercise ball 1 by the user" means both the data representative of the physical activity performed with the exercise ball used as an exercise equipment, for example detecting repetitions, monitoring training time, mobility index, i.e. the analysis of the quality of the movement of the exercise ball with an assessment of the mobility of the user, calories burned, etc., and of the data representative of the physical activity performed with the exercise ball used as a normal seat, for example active time, inactive time, sedentary index, calories burned, type of posture (correct or incorrect), stress index, and so on.

Returning to the embodiment in FIG. 1, it is worth noting that the system 100 may further comprise a display module (not shown in FIG. 1) operatively connected to the first data processing unit 101.

Moreover, in accordance with a further embodiment, alternatively to or in combination with the preceding one, the system 100 may comprise a buzzer (not shown in the figures), for example a microphone, operatively connected to the first data processing unit 101.

In accordance with one embodiment, the first data processing unit 101 is configured to provide the user with the data representative of the use of the exercise ball 1 by the user by means of the display module.

In accordance with another embodiment, the first data processing unit 101 is configured to provide the user with the data representative of the use of the exercise ball 1 by the user by means of the buzzer.

In accordance with another embodiment, the first data processing unit 101 is configured to provide the user with the data representative of the use of the exercise ball 1 by the user by means of the display module and the buzzer.

In accordance with one embodiment, the electronic device 104 comprises the data display module (for example, the display of a smartphone or the screen of a computer).

In accordance with a further embodiment, alternatively to, or in combination with the one described above, the electronic device 104 comprises the buzzer (for example, the speaker of a smartphone or the speaker of a computer).

In accordance with a further embodiment, alternatively to or in combination with the one described above, the monitoring unit 3 of the exercise ball 1 comprises the display module.

In accordance with a further embodiment, alternatively to or in combination with the ones described above, the monitoring unit 3 of the exercise ball 1 comprises the buzzer.

Returning to the system 100 in FIG. 1, in accordance with one embodiment, it is worth noting that the first data processing unit 101 is advantageously configured to determine and provide the user with the user's weight, determined based on said parameters representative of the movement of the exercise ball 1 detected by said at least one sensor 6.

It is worth noting that in this embodiment, such at least one sensor 6 may be for example, a pressure sensor or a deformation sensor.

It is also worth noting that the first data processing unit 101 is configured to calculate the quantities of calories burned by the user in an accurate manner based on the determined weight based on the parameters representative of the movement of the exercise ball 1 detected by said at least one sensor 6.

In accordance with one embodiment, alternatively to or in combination with the ones described above, the first data processing unit 101 is further configured to determine and provide the user with an alert representative of the expiration of a set reference time interval (for example 20 or 30 minutes) for the use of the exercise ball 1, especially if used as a seat.

The set reference time interval is set according to the type of activity performed by the user using the exercise ball 1 as a seat, for example manual work or work by means of computer.

It is worth noting that the expiration of the set reference time interval may be interpreted and used also for communicating to the user to get off the exercise ball (clearly used as a simple seat) and to start a possible movement standing up or may be interpreted and used to communicate to the user to start performing exercises with the exercise ball.

In accordance with a further embodiment, the first data processing unit 101 is further configured to determine and provide the user with information representative of the trend over time of the data representative of the movement of the exercise ball 1 detected by said at least one sensor 6.

In this specific embodiment, such information is preferably provided to the user by means of the display module.

In another embodiment, such information could be provided to the user by means of the buzzer (for example, as an indication that a specific training program is or is not being followed or as an indication that a correct posture on the exercise ball used as a seat is or is not being implemented).

Finally, it is worth noting, in accordance with a further embodiment (not shown in the figures), that the first memory unit 101, the first memory unit 102 and the first data communication module 103 correspond to the second data processing unit 4, the second memory unit 5 and the second data communication module 7, respectively, of the exercise ball 1.

In other words, in this embodiment, the smart monitoring part of the system 100 is integrated into the exercise ball 1.

In particular, in a specific embodiment (not shown in the figures), the monitoring unit 3 of the exercise ball 1 may be capable of receiving the parameters representative of the movement of the exercise ball 1 by the user, determining the data representative of the use of the exercise ball 1 by the user based on such parameters and directly providing the user with such data, if the display module and/or the buzzer are included in the monitoring unit 3 of the exercise ball 1.

In a further embodiment (not shown in the figures), the monitoring unit 3 of the exercise ball 1 may be capable of receiving the parameters representative of the movement of the exercise ball 1 by the user, determining the data representative of the use of the exercise ball 1 by the user based on such parameters and providing the user with such data by means of the display module and/or the buzzer with which the electronic device 104 of the user may be provided.

Figure 3:
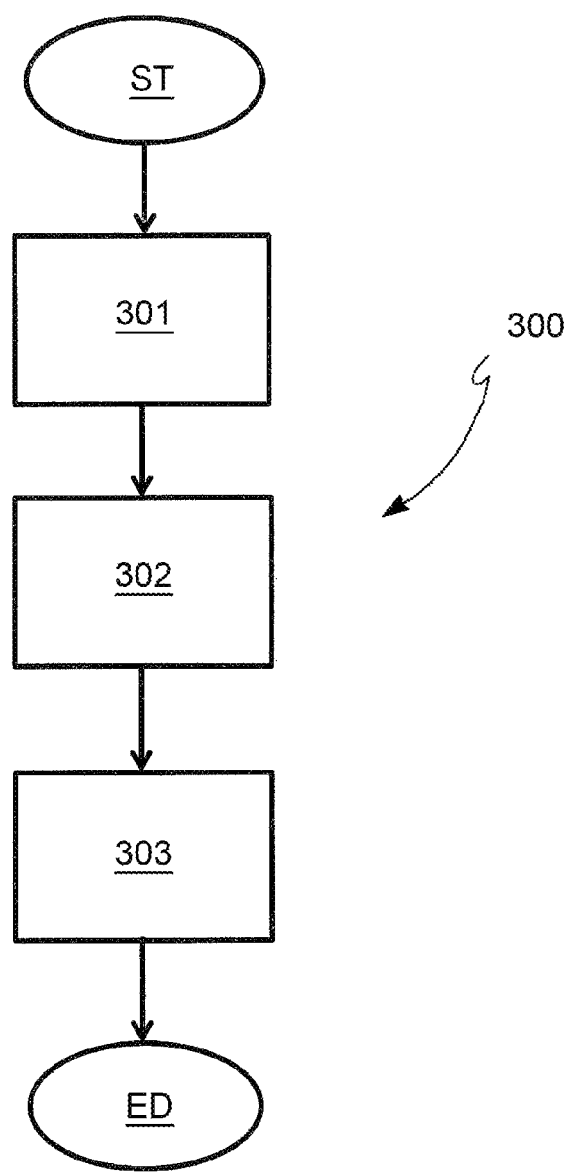
FIG. 3 shows, by means of a block diagram, a method for monitoring the use of an exercise ball by a user.

With reference to the block diagram in FIG. 3, a method 300 for monitoring the use of an exercise ball 1 by a user is now described.

The system 100 and the exercise ball 1 are entirely similar to the ones described above.

The method 300 comprises a symbolic step of starting ST.

The method 300 further comprises a step of detecting 301, by at least one sensor 6 with which the exercise ball 1 is provided, a parameter representative of the movement of the exercise ball 1 by the user.

Such a parameter representative of the movement of the exercise ball 1 by the user and said at least one sensor 6 were defined and described above.

The method 300 further comprises a step of determining 302, by the first data processing unit 101, data representative of the use of the exercise ball 1 by the user based on parameters representative of the movement of the exercise ball 1 by the user detected by said at least one sensor 6.

The method 300 further comprises a step of providing 303 the user, by the first data processing unit 101, with the determined data representative of the use of the exercise ball 1 by the user.

The first data processing unit 101 was described above.

In accordance with one embodiment (not shown in FIG. 3), the method 300 further comprises steps of: determining, by the first data processing unit 101, the user's weight based on said parameters representative of the movement of the exercise ball 1 detected by said at least one sensor 6; and providing the user, by the first data processing unit 101, with the determined user's weight.

In accordance with one embodiment, alternatively to or in combination with the ones described above, the method 300 further comprises steps of: determining, by means of the first data processing unit 101, an alert representative of the expiration of a set reference time interval (for example 20 or 30 minutes) for the use of the exercise ball 1 (especially if it is used as a seat); and providing the user, by the first data processing unit, with such an alert.

The set reference time interval was defined above.

In accordance with a further embodiment, the method 300 further comprises the steps of: determining, by the first data processing unit 101, information representative of the trend over time of the data representative of the movement of the exercise ball 1 detected by said at least one sensor 6; and providing the user, by the first data processing unit 101, with such information.

Returning to the method 300, in accordance with the embodiment in FIG. 3, the method 300 comprises a symbolic step of ending ED.

It is worth noting that in the embodiment in which the first data processing unit 101 is included in the electronic device 104 which can be associated with the user, the steps of the method 300 are intended as being executed by the electronic device 101.

In the embodiment in which the first data processing unit 101 corresponds to the second data processing unit 4 with which the monitoring unit 3 of the exercise ball 1 is provided, the steps of the method 300 are intended as being executed by the exercise ball 1.

In accordance with a further aspect of the present invention, a program product may be loaded into a memory unit (for example, the first memory unit 102 of the electronic device 104 or the second memory unit 5 of the exercise ball 1) of an electronic computer (for example, the first data processing unit 101 of the electronic device 104 or the second data processing unit 4 of the exercise ball 1).

The program product may be executed by the first data processing unit 101 of the electronic computer (electronic device 104) or possibly by the second data processing unit 4 (of the exercise ball 1), if it corresponds with the first data processing unit 101, in order to execute the steps of the method 300 for monitoring the use of the exercise ball 1 by a user, described above with reference to FIG. 3 and according to various further embodiments.

As may be noted, the object of the invention is achieved because the system 100 has the following advantages.

Indeed, parameters representative of the movement of the exercise ball 1 may be obtained with the monitoring unit 3 with which the exercise ball 1 is equipped both when it is used by the user as an exercise equipment and when it is used by the user as a simple seat, while it is possible to determine and provide the user with data representative of the use of the exercise ball 1 by the user both on an electronic device of the user or directly on the exercise ball 1 (in one particular embodiment) with the first data processing unit 101, whether it is integrated into a portable device of the user (for example, a smartphone or a computer) or it is integrated into the monitoring unit 3 of the exercise ball 1.

In other words, immediate feedback may be obtained on the quality both of voluntary physical activity of the user (specific training or rehabilitation program performed with the exercise ball) and of involuntary physical activity (exercise ball 1 used as a seat).

For example, an indication of the stress level of the user may be obtained from the quality of the involuntary physical activity detected, based on a correlation of the stress with the involuntary movements of the user.

In the specific case in which the exercise ball 1 is used as a seat, the system 100 of the invention further allows to have an indication of the time passed during a normal sedentary work activity (manual work or work on a terminal).

Moreover, the system 100 is capable of providing the user also with the user's weight determined according to parameters representative of the movement of the exercise ball 1 detected by said at least one sensor 6.

Finally, the monitoring unit 3 associated with the exercise ball 1 (integrated into the shell 2 or integrated into the cover of the shell 2) also allows to provide this specific type of exercise tool with its own smart electronics.

This appears even more apparent if the exercise ball 1 is used almost exclusively as a simple seat, if also a more sedentary user may learn useful information inherent to the correct use of the exercise ball with the subsequent benefits which may be obtained by a user using the exercise ball as a seat rather than using a common seat or armchair.

Those skilled in the art may make several changes and adaptations to the above-described embodiments of the monitoring system and of related method, and may replace elements with others which are functionally equivalent in order to meet contingent needs, without departing from the scope of the following claims. Each of the features described as belonging to a possible embodiment may be achieved irrespective of the other embodiments described.

The invention claimed is:

1. An exercise ball comprising:
   a shell;
   a monitoring unit operatively associated with the shell, said monitoring unit comprising:
   at least one sensor for detecting a parameter representative of a movement of the exercise ball by a user, and
   a data communication module adapted to communicate said parameter representative of the movement of the exercise ball by the user to a first data processing unit by a wireless data communication channel,
   wherein the exercise ball is arranged to be used as an exercise equipment for performing physical exercise in accordance with a training or rehabilitation program and to be used as a seat for improving posture and performing exercises for muscle reinforcement and balance,
   wherein the movement of the exercise ball by the user to be detected by the at least one sensor is representative of the use of the exercise ball as exercise equipment for performing physical exercise in accordance with a training or rehabilitation program or is representative of the use of the exercise ball as a seat for improving posture and performing exercises for muscle reinforcement and balance,
   wherein the monitoring unit further comprises a second data processing unit, the second data processing unit being configured to determine and provide the user with the user's weight, determined based on the parameter representative of the movement of the exercise ball detected by the at least one sensor,
   wherein the second data processing unit is further configured to determine and provide the user with an alert representative of an expiration of a set reference time interval for the use of the exercise ball.

2. The exercise ball according to claim 1, wherein the monitoring unit of the exercise ball is integrated into the shell of the exercise ball.

3. The exercise ball according to claim 2, wherein the shell comprises a hole configured to introduce pressurized air into the shell, such hole being provided with a closing valve such that the shell filled with air configured to maintain the shape, the monitoring unit being associated with or integrated into a portion of the shell wherein the hole is present with the closing valve.

4. The exercise ball according to claim 3, wherein the monitoring unit is associated with or integrated into the closing valve of the hole of the shell.

5. The exercise ball according to claim 3, wherein said closing valve is configured to adjust the pressure of the air inside the shell so as to selectively inflate and deflate the exercise ball.

6. The exercise ball according to claim 3, wherein the monitoring unit is associated with or integrated into a further portion of the shell, different from the portion of the shell in which there is the hole with the closing valve.

7. The exercise ball according to claim 1, wherein the exercise ball comprises a cover of the shell, the monitoring unit being integrated into the cover of the shell of the exercise ball.

8. The exercise ball according to claim 7, wherein the monitoring unit is associated with or integrated into a portion of the cover intended to cover the portion of the shell of the exercise ball in which there is the hole with the closing valve, at which the deformation of the shell due to the action of the user is consistent.

9. The exercise ball according to claim 7, wherein the monitoring unit comprises a first portion integrated into the shell of the exercise ball, and a second portion integrated into the cover of the shell of the exercise ball.

10. The exercise ball according to claim 1, wherein the monitoring unit of the exercise ball is configured to:
    receive parameters representative of the movement of the exercise ball by the user;
    determine the data representative of the use of the exercise ball by the user based on said parameters.

11. The exercise ball according to claim 10, wherein the monitoring unit is further configured to provide the user with said data representative of the use of the exercise ball by the user.

12. The exercise ball according to claim 1, wherein the shell comprises a stabilizing element adapted to allow a portion of the exercise ball to rest on the floor.

13. The exercise ball according to claim 1, wherein, if the parameter to be detected is a parameter representative of the movement of the exercise ball, the at least one sensor is at least one of an accelerometer and a gyroscope.

14. The exercise ball according to claim 1, wherein, if the parameter to be detected is a parameter representative of the deformation of the shell under the action of the user, the at least one sensor is at least one of an extensometer and a pressure sensor.

15. The exercise ball according to claim 1, wherein the exercise ball comprises a plurality of sensors, each for detecting a parameter representative of the movement of the exercise ball by the user.

16. The exercise ball according to claim 1, wherein the monitoring unit of the exercise ball comprises a display module.

17. The exercise ball according to claim 1, wherein the monitoring unit of the exercise ball comprises a buzzer.

18. The exercise ball according to claim 1, wherein the first data processing unit is further configured to determine and provide the user with information representative of a trend over time of the data representative of the movement of the exercise ball detected by said at least one sensor.

* * * * *